United States Patent
Feng et al.

(10) Patent No.: US 9,233,190 B2
(45) Date of Patent: *Jan. 12, 2016

(54) CULTURE SUBSTRATE COMPRISING CARBON NANOTUBE STRUCTURE

(75) Inventors: Chen Feng, Beijing (CN); Li Fan, Beijing (CN); Wen-Mei Zhao, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/349,656

(22) Filed: Jan. 13, 2012

(65) Prior Publication Data

US 2012/0196368 A1    Aug. 2, 2012

(30) Foreign Application Priority Data

Jan. 28, 2011    (CN) .......................... 2011 1 0031676
Apr. 21, 2011   (CN) .......................... 2011 1 0100912

(51) Int. Cl.
    *C12N 5/0793*    (2010.01)
    *A61L 27/38*     (2006.01)
    *B82Y 5/00*      (2011.01)

(52) U.S. Cl.
    CPC ........... *A61L 27/3895* (2013.01); *A61L 27/383* (2013.01); *B82Y 5/00* (2013.01)

(58) Field of Classification Search
    CPC ........... A61L 2/0011; A61L 2/08; A61L 2/14; A61L 27/383; A61L 27/422; A61L 2400/12; A61L 2430/32; A61L 27/3895; A61L 27/08; A61L 27/34; A61N 1/205; A61N 1/37252; B82Y 5/00; B82Y 10/00; B82Y 15/00; B82Y 20/00; B82Y 30/00; B82Y 40/00; B82Y 99/00
    See application file for complete search history.

(56) References Cited

U.S. PATENT DOCUMENTS

| | | | |
|---|---|---|---|
| 7,931,683 B2 | 4/2011 | Weber et al. | |
| 2004/0053780 A1 | 3/2004 | Jiang et al. | |
| 2005/0163924 A1 | 7/2005 | Anderson et al. | |
| 2005/0181143 A1* | 8/2005 | Zhang et al. | 427/532 |
| 2007/0015277 A1 | 1/2007 | Hattori et al. | |
| 2007/0166223 A1 | 7/2007 | Jiang et al. | |
| 2007/0243124 A1* | 10/2007 | Baughman et al. | 423/447.1 |
| 2008/0140195 A1 | 6/2008 | Su et al. | |
| 2008/0170982 A1* | 7/2008 | Zhang et al. | 423/447.3 |
| 2008/0248235 A1 | 10/2008 | Feng et al. | |
| 2008/0299031 A1 | 12/2008 | Liu et al. | |
| 2009/0068448 A1 | 3/2009 | Liu et al. | |
| 2009/0138077 A1 | 5/2009 | Weber et al. | |
| 2009/0160796 A1* | 6/2009 | Jiang et al. | 345/173 |
| 2009/0181239 A1* | 7/2009 | Fan et al. | 428/327 |
| 2009/0301993 A1 | 12/2009 | Feng et al. | |
| 2010/0019209 A1 | 1/2010 | Meng et al. | |
| 2010/0124622 A1 | 5/2010 | Wang et al. | |
| 2010/0144004 A1 | 6/2010 | Zhong et al. | |
| 2012/0150317 A1 | 6/2012 | Fan et al. | |

FOREIGN PATENT DOCUMENTS

| | | |
|---|---|---|
| CN | 1694851 | 11/2005 |
| CN | 1833618 | 9/2006 |
| CN | 101186447 | 5/2008 |
| CN | 101196514 | 6/2008 |
| CN | 101239712 | 8/2008 |
| CN | 101256166 | 9/2008 |
| CN | 101284662 | 10/2008 |
| CN | 101381071 | 3/2009 |
| CN | 101597049 | 12/2009 |
| CN | 101643702 | 2/2010 |
| CN | 101582302 | 12/2011 |
| CN | 102551916 | 8/2014 |
| JP | 5-277944 | 10/1993 |
| JP | 2004-107196 | 4/2004 |
| JP | 2006-94720 | 4/2006 |
| JP | 2007-20444 | 2/2007 |
| JP | 2007-161563 | 6/2007 |
| JP | 2008-523254 | 7/2008 |
| JP | 2008-297195 | 12/2008 |
| JP | 2010-115778 | 5/2010 |
| JP | 2010-534518 | 11/2010 |
| TW | 201022140 | 6/2010 |
| WO | WO 2008004990 A2 * | 1/2008 |
| WO | WO2009018029 | 2/2009 |

OTHER PUBLICATIONS

Nguyen-Vu, T.D.B. et al., Vertically Aligned Carbon Nanofiber Architecture as a Multifunctional 3-D Neural Electrical Interface, IEEE Transactions on Biomedical Engineering, 2007, vol. 54, No. 6, pp. 1121-1128.*

Li J. et al., Bottom-up approach for carbon nanotube interconnects, Applied Physics Letters, 2003, vol. 82, No. 15, pp. 2491-2493.*

Wei B.Q. et al., Assembly of Highly Organized Carbon Nanotube Architectures by Chemical Vapor Deposition, Chem. Mater., 2003, vol. 15, No. 8, pp. 1598-1606.*

Zhang X. et al., Guided neurite growth on patterned carbon nanotubes, Sensors and Actuators B, 2005, vol. 106, pp. 843-850.*

Wang K. et al., Neural Stimulation with a Carbon Nanotube Microelectrode Array, Nano Letters, 2006, vol. 6, No. 9, pp. 2043-2048.*

Liu K. et al., Controlled Growth of Super-Aligned Carbon Nanotube Arrays for Spinning Continuous Unidirectional Sheets with Tunable Physical Properties, Nano Letters, 2008, vol. 8, No. 2, pp. 700-705.*

(Continued)

*Primary Examiner* — Satyendra K Singh
(74) *Attorney, Agent, or Firm* — Novak Druce Connolly Bove + Quigg LLP

(57) ABSTRACT

A culture medium includes a carbon nanotube structure and a hydrophilic layer. The culture medium is capable of culturing at least one neuron. The hydrophilic layer has a polar surface and is located on a surface of the carbon nanotube structure. The polar surface is located on a surface of the hydrophilic layer away from the carbon nanotube structure, and has a polarity attracted to a polarity of the at least one neuron.

3 Claims, 11 Drawing Sheets

(56) References Cited

OTHER PUBLICATIONS

Armitage N.P. et al., Quasi-Langmuir-Blodgett Thin Film Deposition of Carbon Nanotubes, Jul. 29, 2003; published online in ArXiv at the web at: arXiv:cond-mat/0307712v1 [cond-mat.mtrl-sci], pp. 1-3.*
Seidlits S.K. et al., Nanostructured scaffolds for neural applications (a Review), Nanomedicine, 2008, vol. 3, No. 2, pp. 183-199.*
Sunden E.O. "Carbon Nanotube Synthesis for Microsystems Applications", a Master's Thesis for the degree of Maste of Science in Mechanical Engineering, presented on Aug. 2006 to Georgia Institute of Technology, pp. i-xvi, and 1-111.*
Galvan-Garcia P. et al., Robust cell migration and neuronal growth on pristine carbon nanotube sheets and yarns, J. Biomater. Sci. Polymer Edn., 2007, vol. 18, No. 10, pp. 1245-1261.*
Peluso G. et al., Polyetherimide as biomaterial: Preliminary in vitro and in vivo biocompatibility testing, Journal of Materials Science: Materials in Medicine, 1994, vol. 5, pp. 738-742.*
Li X. et al., Effect of carbon nanotubes on cellular functions in vitro, J. Biomed. Mater. Res., 2009, vol. 91A, pp. 132-139.*
Xuan Zhang et al, "Guided neurite growth on patterned carbon nanotubes" Sensors and Actuators B106(2005)843-850.
T. D. BarbaraNguyen-Vu et al,"Vertically Aligned Carbon NanofiberArchitecture as a Multifunctional 3-D Neural Electrical Interface"EEETRANS Actions Onbiome Dical Engineering, vol. 54, No. 6,Jun. 2007.
Ke Wang et al, "Neural Stimulation with a Nanotube Microelectrode Array" Nano Letters,vol. 6,No. 9,p. 2043-2048, 2006.
Hui Hu et al,"Polyethyeneimine Functionalized Single-Walled Carbon Nanotubes as a Substrate for Neuronal Growth",J. Phys.Chem. B,vol. 109, p. 4285-4289, Feb. 22, 2005.
Hui Hu et al, "Chemically Functionalized Carbon Nanotubes as a Substrate for Neuronal Growth" Nano Letters,vol. 4, No. 3,p. 507-511,Feb. 18, 2004.
Yingchun Ni et al, "Chemically Functionalized Water Soluble Single-Walled Carbon Nanotubes Modulate Neurite Outgrowth" Journal of Nanoscience and Nanotechnology, vol. 5,p. 1707-1712,2005.
Hua Ai et al, "Biocompatibility of layer-by-layer self-assembled nanofilm on silicone rubber for nenurons" Journal of Neuroscience Methods,vol. 128 1-17,p. 1-8,2003.
Cassell,A.M. et al, "Vertically aligned carbon nanofibers: interconnecting solid state electronics with biosystems", J Nanosci Nanotechnol, 2009, vol. 9, No. 8, p. 5038-5046.
Jun Li et al,"Bottom-up approach for carbon nanotube interconnects", Applied Physics Letters,2003,vol. 82, p. 2491-2493.
Jiangtao Di and Qingwen Li."Well-Aligned and Conductive Carbon-Nanotube/TIO2 Film for Flexible Photoelectrode";World Journal of Engineering;2010,supplement 3,pp. 273-274.
Sunden,E,O, "Carbon nanotubes synthesis for microsystems application", Georgia Institute of Techinology, 2006.
Mel Zhang et al., "Strong Transparent, Multifunctional, Carbon Nanotube Sheets", Science, America, AAAS, vol. 309, pp. 1215-1219, Aug. 19, 2005.
Xuan Zhang et al., "Guided neurite growth on patterned carbon nanotubes", Sensors and Actuators B, pp. 843-850, 2005.
Kaili Jiang et al., "Spinning continuous carbon nanotube yarns", Nature, vol. 419, pp. 801, 2002.
"Spinning continuous carbon nanotube yarns", Nature, 2002, vol. 419, No. 6909, p. 801.

* cited by examiner

CULTURE SUBSTRATE COMPRISING CARBON NANOTUBE STRUCTURE

This application claims all benefits accruing under 35 U.S.C. §119 from China Patent Application No. 201110031676.3, filed on Jan. 28, 2011 and China Patent Application No. 201110100912.2, filed on Apr. 21, 2011 in the China Intellectual Property Office, disclosure of which is incorporated herein by reference.

CROSS-REFERENCES TO RELATED APPLICATIONS

This application is related to commonly-assigned application Ser. No. 13/349,582, entitled, "NERVE GRAFT," filed on Jan. 13, 2012, Ser. No. 13/349,577, entitled, "METHOD FOR FORMING NERVE GRAFT," filed on Jan. 13, 2012, and Ser. No. 13/349,660, entitled, "METHOD FOR FORMING CULTURE MEDIUM," filed on Jan. 13, 2012.

BACKGROUND

1. Technical Field

The present disclosure relates to a culture medium, especially to a culture medium for culturing neurons.

2. Description of Related Art

A nervous system is a complex cellular communication network that is mainly composed of neurons and glial cells (neuroglial cells). Glial cells occupy spaces between the neurons and modulate the neurons' functions. The neurons sense stimuli and transmit this information to the brain for processing and storage. For example, the neurons receive diverse stimuli from the environment (e.g. light, touch, sound) and transmit electrical signals, which are then converted into chemical signals to be passed on to other cells.

Neurons exist in a number of different shapes and sizes, and can be classified by their morphology and function. The basic morphology of a neuron includes a cell body and neurites projecting/branching from the cell body towards other neurons. The neurites can also be divided into two types by their functions. One is a dendrite, which branches around the cell body and receive signals from other neurons to the cell body. The other is an axon, which branches from the cell body and grows continually without tapering. The axon conducts the signals away from the neuron's cell body. The end of the axon has branching terminals that release neurotransmitters into a gap between the branching terminals and the dendrites of other neurons. Thus, the information or signal is propagated.

Neuron damage can lead to neurite degeneration and retraction. If the damage is severe, breaks in neurites affect signal transmission and the cellular communication between neurons will cease.

What is needed, therefore, is a culture medium for culturing neurons which can reconnect opposite terminals in broken neurites.

BRIEF DESCRIPTION OF THE DRAWINGS

Many aspects of the disclosure can be better understood with reference to the drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
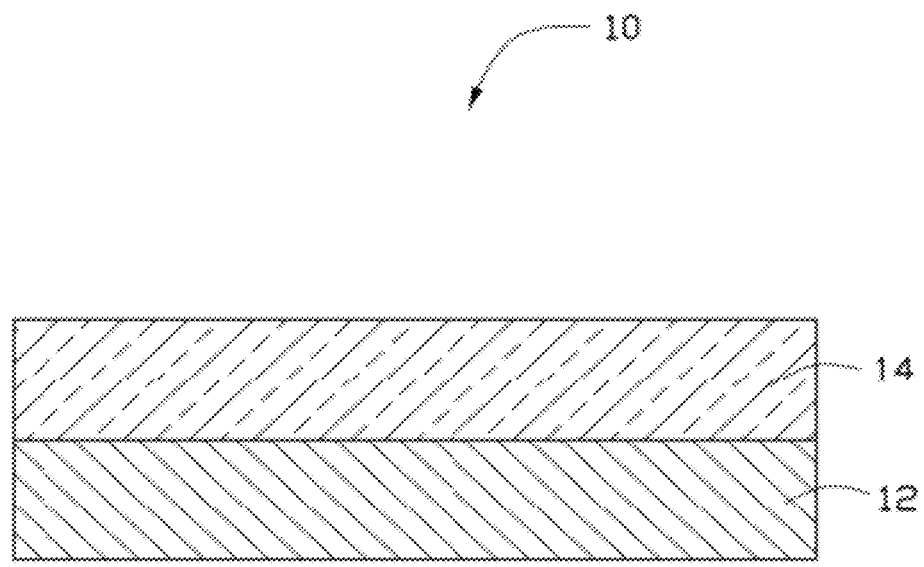
FIG. 1 is a cross-sectional view of one embodiment of a culture medium.

Referring to FIG. 1, one embodiment of a culture medium 10 includes a carbon nanotube structure 12 and a hydrophilic layer 14. The hydrophilic layer 14 is located on a surface of the carbon nanotube structure 12.

The hydrophilic layer 14 is a hydrophilic environment for growing a number of neurons. The thickness of the hydrophilic layer 14 is in a range from about 1 nanometer (nm) to about 100 nm. Preferably, the hydrophilic layer 14 has a thickness in a range from about 1 nm to about 50 nm. The hydrophilic layer 14 is made from inorganic materials, such as silicon dioxide, titanium dioxide, iron oxide, or any combination thereof. In one embodiment, the hydrophilic layer 14 is a silicon dioxide layer with a thickness about 10 nm.

The carbon nanotube structure 12 is capable of forming a free-standing structure. The term "free-standing structure" can be defined as a structure that does not need to be supported by a substrate. For example, a free-standing structure can sustain the weight of itself if the free-standing structure is hoisted by a portion thereof without any significant damage to its structural integrity. Carbon nanotubes distributed in the carbon nanotube structure 12 defines a plurality of gaps therebetween. The carbon nanotubes can have a significant van der Waals attractive force therebetween. The free-standing structure of the carbon nanotube structure 12 is realized by the carbon nanotubes joined by van der Waals attractive force.

The carbon nanotubes in the carbon nanotube structure 12 can be orderly or disorderly arranged. The term 'disordered carbon nanotube film structure' includes, but is not limited to, a structure where the carbon nanotubes are arranged along many different directions such that the number of carbon nanotubes arranged along each different direction can be almost the same (e.g. uniformly disordered), and/or entangled with each other. The term 'ordered carbon nanotube film structure' includes, but is not limited to, a structure where the carbon nanotubes are arranged in a consistently systematic manner, e.g., the carbon nanotubes are arranged approximately along a same direction and or have two or more sections within each of which the carbon nanotubes are arranged approximately along a same direction (different sections can have different directions). The carbon nanotubes in the carbon nanotube structure 12 can be single-walled, double-walled, and/or multi-walled carbon nanotubes.

Figure 2:
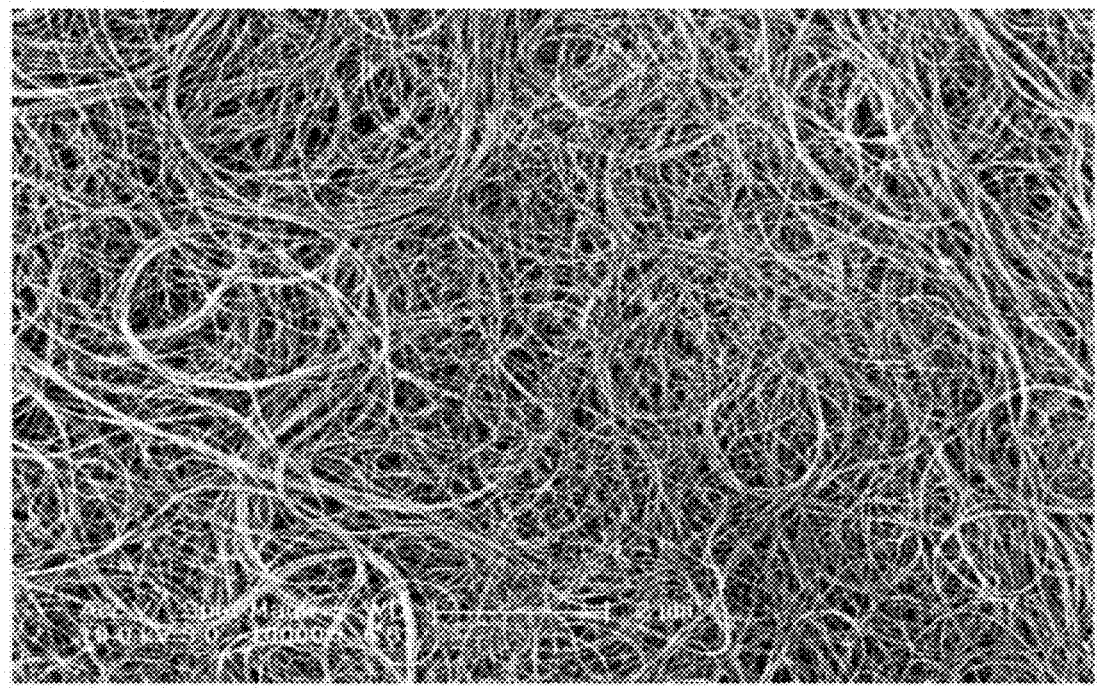
FIG. 2 shows a scanning electron microscope (SEM) image of a flocculated carbon nanotube film.

The carbon nanotube structure 12 can include a flocculated carbon nanotube film as shown in FIG. 2. The flocculated carbon nanotube film can include a number of long, curved, disordered carbon nanotubes entangled with each other and can form a free-standing structure. Furthermore, the flocculated carbon nanotube film can be isotropic. The carbon nanotubes can be substantially uniformly dispersed in the flocculated carbon nanotube film. The adjacent carbon nanotubes are acted upon by the van der Waals attractive force therebetween, thereby forming an entangled structure with micropores defined therein. Alternatively, the flocculated carbon nanotube film is porous. Sizes of the micropores can be in a range from about 1 nm to about 500 nm. Due to the carbon nanotubes in the carbon nanotube structure 12 being entangled with each other, the carbon nanotube structure 12 employing the flocculated carbon nanotube film has excellent durability and can be fashioned into desired shapes with a low risk to the integrity of the carbon nanotube structure 12. The flocculated carbon nanotube film, in some embodiments, will not require the use of a structural support due to the carbon nanotubes being entangled and adhered together by van der Waals attractive force therebetween.

Figure 3:
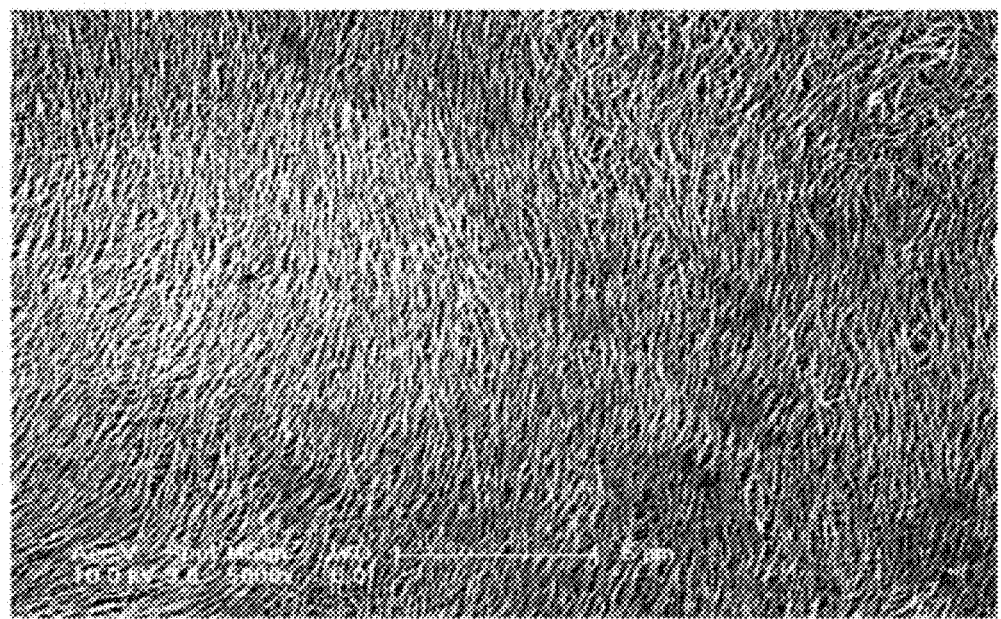
FIG. 3 shows an SEM image of a pressed carbon nanotube film.

The carbon nanotube structure 12 can include a pressed carbon nanotube film. The carbon nanotubes in the pressed carbon nanotube film can be arranged along a same direction or arranged along different directions. The carbon nanotubes in the pressed carbon nanotube film can rest upon each other. The adjacent carbon nanotubes are combined and attracted to each other by van der Waals attractive force, and can form a free-standing structure. An angle between a primary alignment direction of the carbon nanotubes and a surface of the pressed carbon nanotube film can be in a range from about 0 degrees to about 15 degrees. The pressed carbon nanotube film can be formed by pressing a carbon nanotube array. The angle is closely related to pressure applied to the carbon nanotube array. The greater the pressure, the smaller the angle. The carbon nanotubes in the carbon nanotube film are substantially parallel to the surface of the carbon nanotube film if the angle is about 0 degrees. A length and a width of the carbon nanotube film can be set as desired. The pressed carbon nanotube film can include a number of carbon nanotubes substantially aligned along one or more directions. The pressed carbon nanotube film can be obtained by pressing the carbon nanotube array with a pressure head. Alternatively, the shape of the pressure head and the pressing direction can determine the direction of the carbon nanotubes arranged therein. Specifically, in one embodiment, a planar pressure head is used to press the carbon nanotube array along the direction substantially perpendicular to a substrate. A number of carbon nanotubes pressed by the planar pressure head may be sloped in many directions. In one embodiment, as shown in FIG. 3, if a roller-shaped pressure head is used to press the carbon nanotube array along a certain direction, the pressed carbon nanotube film having a number of carbon nanotubes substantially aligned along the certain direction can be obtained. In another embodiment, if the roller-shaped pressure head is used to press the carbon nanotube array along different directions, the pressed carbon nanotube film having a number of carbon nanotubes substantially aligned along different directions can be obtained.

Figure 4:
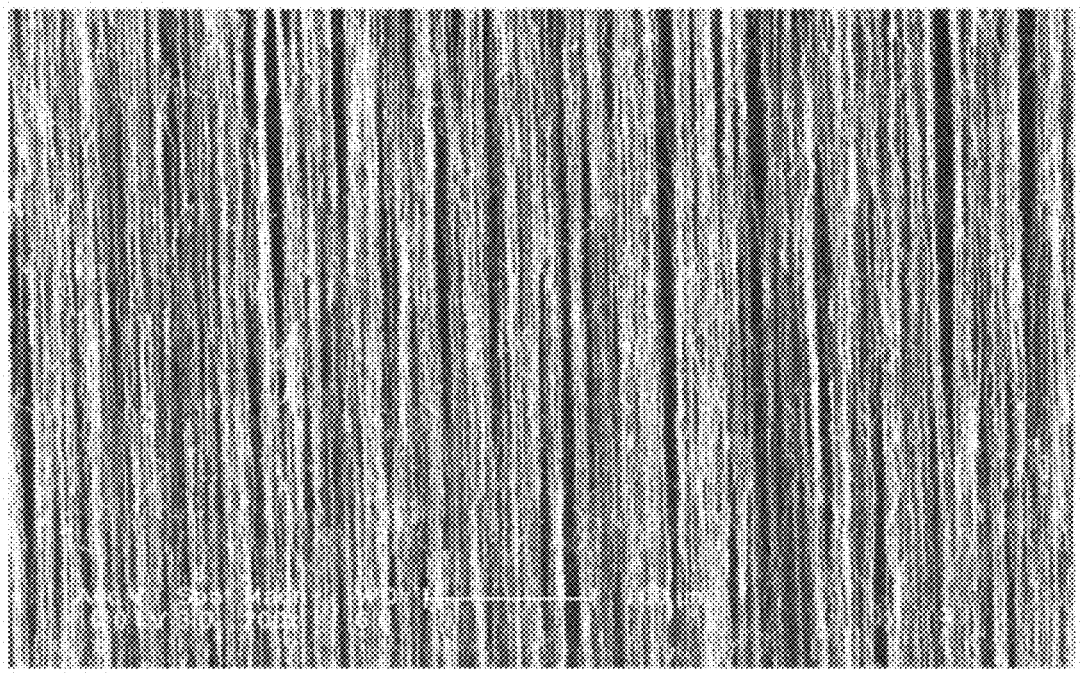
FIG. 4 shows an SEM image of a drawn carbon nanotube film.

In one embodiment, the carbon nanotube structure 12 includes at least one drawn carbon nanotube film as shown in FIG. 4. The drawn carbon nanotube film can have a thickness of about 0.5 nm to about 100 micrometers (μm). The drawn carbon nanotube film includes a number of carbon nanotubes that can be arranged substantially parallel to a surface of the drawn carbon nanotube film. A plurality of micropores having a size of about 1 nm to about 500 nm can be defined by the carbon nanotubes. A large number of the carbon nanotubes in the drawn carbon nanotube film can be oriented along a preferred orientation, meaning that a large number of the carbon nanotubes in the drawn carbon nanotube film are arranged substantially along the same direction. An end of one carbon nanotube is joined to another end of an adjacent carbon nanotube arranged substantially along the same direction, by van der Waals attractive force. More specifically, the drawn carbon nanotube film includes a number of successively oriented carbon nanotube segments joined end-to-end by van der Waals attractive force therebetween. Each carbon nanotube segment includes a number of carbon nanotubes substantially parallel to each other and joined by van der Waals attractive force therebetween. The carbon nanotube segments can vary in width, thickness, uniformity, and shape. A small number of the carbon nanotubes are randomly arranged in the drawn carbon nanotube film and has a small if not negligible effect on the larger number of the carbon nanotubes in the drawn carbon nanotube film arranged substantially along the same direction.

Figure 5:
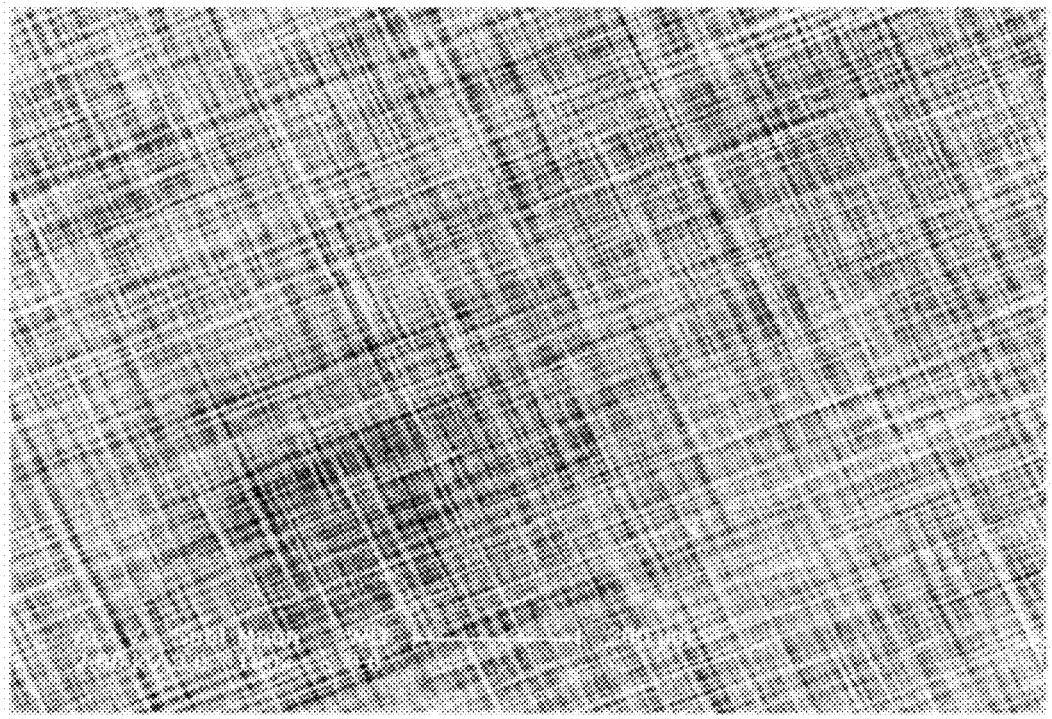
FIG. 5 shows an SEM image of a carbon nanotube structure.

In another embodiment, the carbon nanotube structure 12 can include a number of stacked drawn carbon nanotube films as shown in FIG. 5. Adjacent drawn carbon nanotube films can be adhered by only the van der Waals attractive force therebetween. An angle can exist between the carbon nanotubes in adjacent drawn carbon nanotube films. The angle between the aligned directions of the adjacent drawn carbon nanotube films can be in a range from about 0 degrees to about 90 degrees. In one embodiment, the carbon nanotube structure 12 is formed by 30 layers of drawn carbon nanotube films. The angle between the aligned directions of the adjacent drawn carbon nanotube films is about 90 degrees. Simultaneously, aligned directions of adjacent drawn carbon nanotube films can be substantially perpendicular to each other, thus a plurality of micropores and nodes can be defined by the carbon nanotube structure 12.

Figure 6:
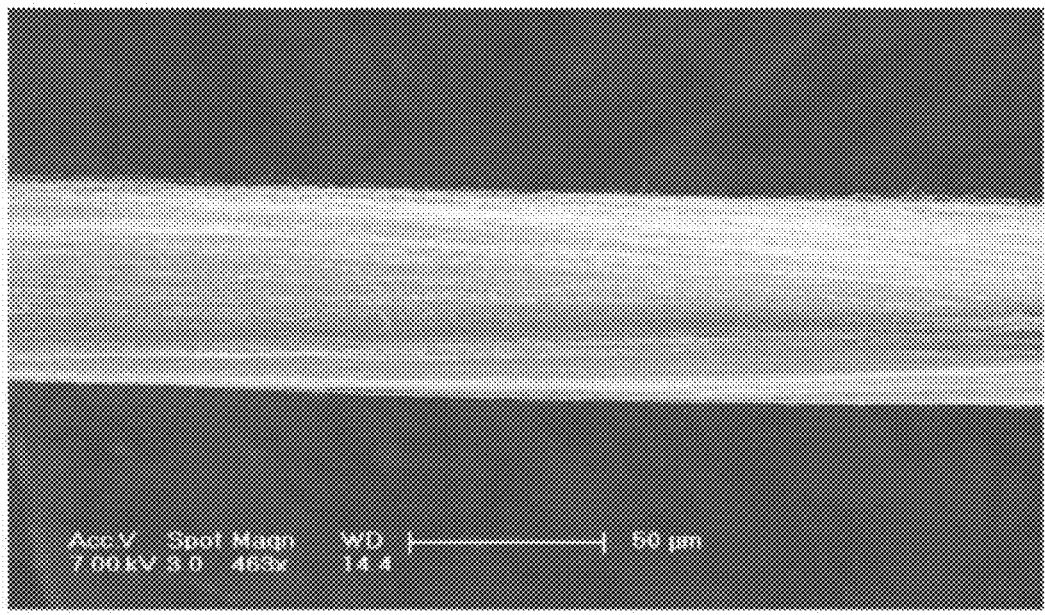
FIG. 6 shows an SEM image of an untwisted carbon nanotube wire.

Alternatively, the carbon nanotube structure 12 can be formed by a number of carbon nanotube wires. Thus, one portion of the carbon nanotube wires is arranged substantially parallel to each other and extends substantially along a first direction. In addition, the other portion of the carbon nanotube wires is arranged substantially parallel to each other and extends substantially along a second direction. The first direction and the second direction can be substantially perpendicular to each other. In one embodiment, the carbon nanotube wire can be classified as untwisted carbon nanotube wire and twisted carbon nanotube wire. Referring to FIG. 6, the untwisted carbon nanotube wire is made by treating an organic solvent to the carbon nanotude film described above. In such case, the carbon nanotubes of the untwisted carbon nanotube wire are substantially parallel to the axis of the carbon nanotube wire. In one embodiment, the organic solvent can be ethanol, methanol, acetone, dichloroethane, or chloroform. The diameter of the untwisted carbon nanotube wire is in a range from about 0.5 nm to about 1 millimeter.

Figure 7:
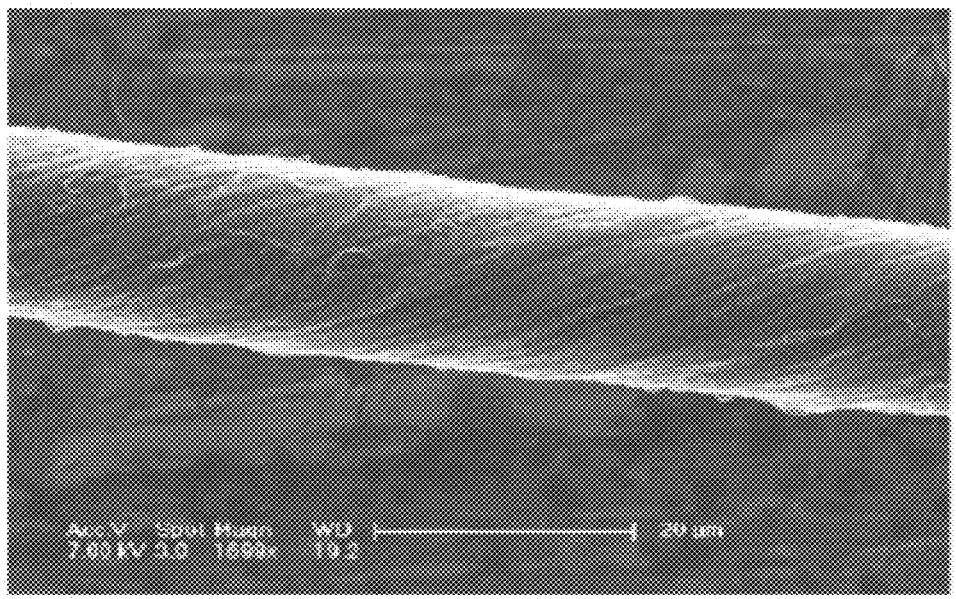
FIG. 7 shows an SEM image of a twisted carbon nanotube wire.

Furthermore, referring to FIG. 7, the carbon nanotube wire can be formed by twisting the carbon nanotube film to form the twisted carbon nanotube wire. Specifically, twisted carbon nanotube wire is formed by turning two opposite ends of the carbon nanotube film in opposite directions. In one embodiment, the carbon nanotubes of the carbon nanotube wire are aligned around the axis of the carbon nanotube spirally.

The culture medium 10 can define a growth surrounding the neurons, thus the nerve network can be formed on the culture medium 10. Both of the hydrophilic layer 14 and the carbon nanotube structure 12 can have good tactility, and nonmetal and bio-compatible properties. Thus, the culture medium 10 including the hydrophilic layer 14 and the carbon nanotube structure 12 can be transplanted into a biological body and form a shape as desired. The shape and a thickness of the culture medium 10 can be designed as a shape and a thickness of a wound on the biological body. The neurons of the nerve network can communicate with each other, thus, if the culture medium 10 with the nerve network is transplanted into the wound, neurons of the biological body close to the wound can communicate with and connect to the nerve network. Thus, the injured neurons can be reconnected together. In one embodiment, an area of a surface of the carbon nanotube structure 12 is greater than 15×15 square millimeters.

Figure 8:
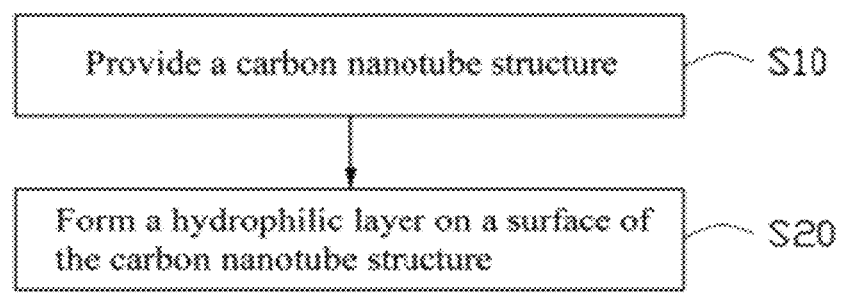
FIG. 8 is a flow chart of one embodiment of a method for forming a culture medium.

Referring to FIG. 8, a method for forming a culture medium includes the steps of:

S10, providing a carbon nanotube structure; and

S20, forming a hydrophilic layer on a surface of the carbon nanotube structure

In the step S10, the carbon nanotube structure has a number of carbon nanotubes capable of forming a free-standing structure. The free-standing structure of the carbon nanotube structure is realized by the carbon nanotubes joined by van der Waals attractive force. The carbon nanotube structure can include at least one carbon nanotube film. The carbon nanotube film can be a flocculated carbon nanotube film as shown in FIG. 2, a pressed carbon nanotube film as shown in FIG. 2, or a drawn carbon nanotube film as shown in FIG. 4. In addition, the carbon nanotube structure can include at least one carbon nanotube wire. The carbon nanotube wire can be an untwisted carbon nanotube wire as shown in FIG. 6 or a twisted carbon nanotube wire as shown in FIG. 7. In one embodiment, the carbon nanotube structure is formed by 30 layers of drawn carbon nanotube films. The angle between the aligned directions of the adjacent drawn carbon nanotube films is substantially 90 degrees.

In the step S20, the hydrophilic layer is formed on the surface of the carbon nanotube structure by evaporation or sputtering. The hydrophilic layer is capable of culturing a number of neurons. The material of the hydrophilic layer is hydrophilic. For example, the hydrophilic layer is made from inorganic materials, such as silicon dioxide, titanium dioxide, iron oxide, or any combination thereof. In one embodiment, the carbon nanotube structure formed by 30 layers of drawn carbon nanotube films is fixed at a frame, and then a silicon dioxide layer is formed on the surface of the carbon nanotube structure by electron beam evaporation.

The carbon nanotube structure can be sterilized. Sterilizing the carbon nanotube structure kills all of the bacteria distributed in the carbon nanotube structure. The carbon nanotube structure can be sterilized by means of an ultraviolet sterilization technology or a high temperature sterilization technology.

Figure 9:
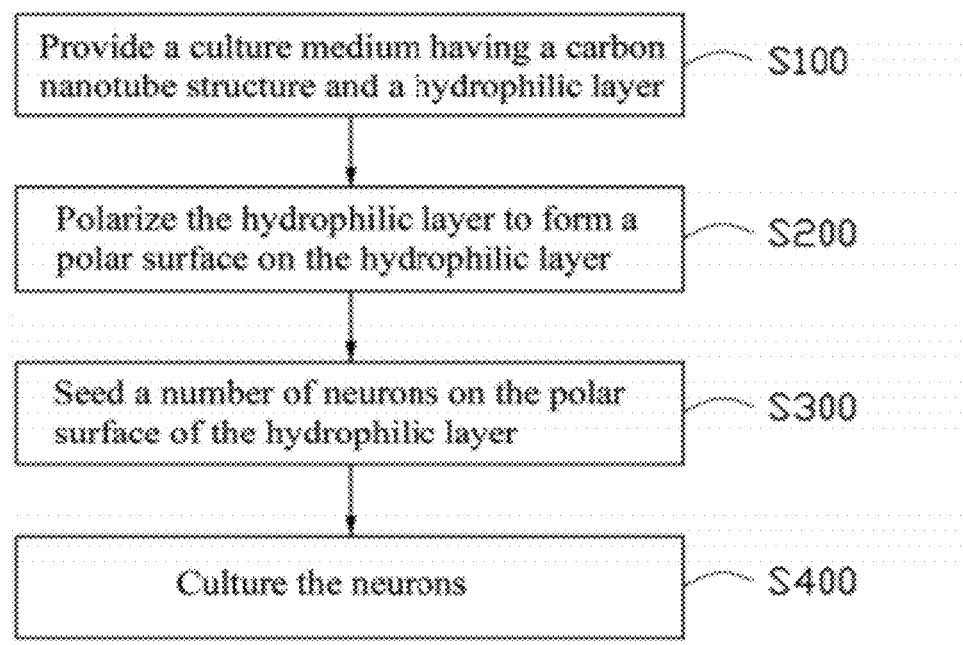
FIG. 9 is a flowchart of one embodiment of a method for culturing a number of neurons.

Referring to FIG. 9, a method for culturing a number of neurons includes the steps of:

S100, providing a culture medium having a carbon nanotube structure and a hydrophilic layer formed on a surface of the carbon nanotube structure;

S200, polarizing the hydrophilic layer to form a polar surface on the hydrophilic layer;

S300, seeding a number of neurons on the polar surface of the hydrophilic layer; and S400, culturing the neurons.

In the step S200, the polar surface can be formed on the hydrophilic layer by the steps of:

(a1), providing a supporter;

(b1), placing the carbon nanotube structure having the hydrophilic layer on a surface of the supporter; and (c1), forming the polar surface on the hydrophilic layer by soaking the carbon nanotube structure having the hydrophilic layer on the supporter.

In step (b1), the carbon nanotube structure can be located on part of the surface of the supporter. To decrease a specific surface area of the carbon nanotube structure and increase an adhesive attraction force between the carbon nanotube structure and the supporter, the step (b1) can further include the following steps: (b11), soaking the carbon nanotube structure on the surface of the supporter with an organic solvent; and (b12), evaporating the organic solvent from the carbon nanotube structure. In one embodiment, the supporter is a plastic petri dish or an observation dish.

In step (c1), the carbon nanotube structure can be soaked with a polyamino acid solution or a polyetherimide solution to form the polar surface on the hydrophilic layer. For example, the polyamino acid solution or the polyetherimide solution can be sprayed on the surface of the hydrophilic layer. In one embodiment, to soak the hydrophilic layer with the polyamino acid solution or the polyetherimide solution, the step (c1) includes the following steps: (c11), dripping the polyamino acid solution or the polyetherimide solution on the surface of the hydrophilic layer; and (c12), purging the polyamino acid solution or the polyetherimide solution from the hydrophilic layer with deionized water after the polar surface is formed on the hydrophilic layer. In one embodiment, the polyamino acid solution is dripped on the carbon nanotube structure for about 10 hours. A concentration of the polyamino acid solution can be about 20 milligrams per milliliter.

In the step S300, the neurons can be from a mammal, such as a human, a mouse, or a cow. In one embodiment, the neurons are hippocampal neurons from a mouse. The neurons can be seeded on the hydrophilic layer by spraying a neuron solution to the polar surface of the hydrophilic layer, or by dipping the culture substrate into the neuron solution. In one embodiment, when the polar surface of the hydrophilic layer is covered by the neuron solution, the neurons in the neuron solution can be deposited or seeded on the polar surface of the hydrophilic layer.

Figure 10:
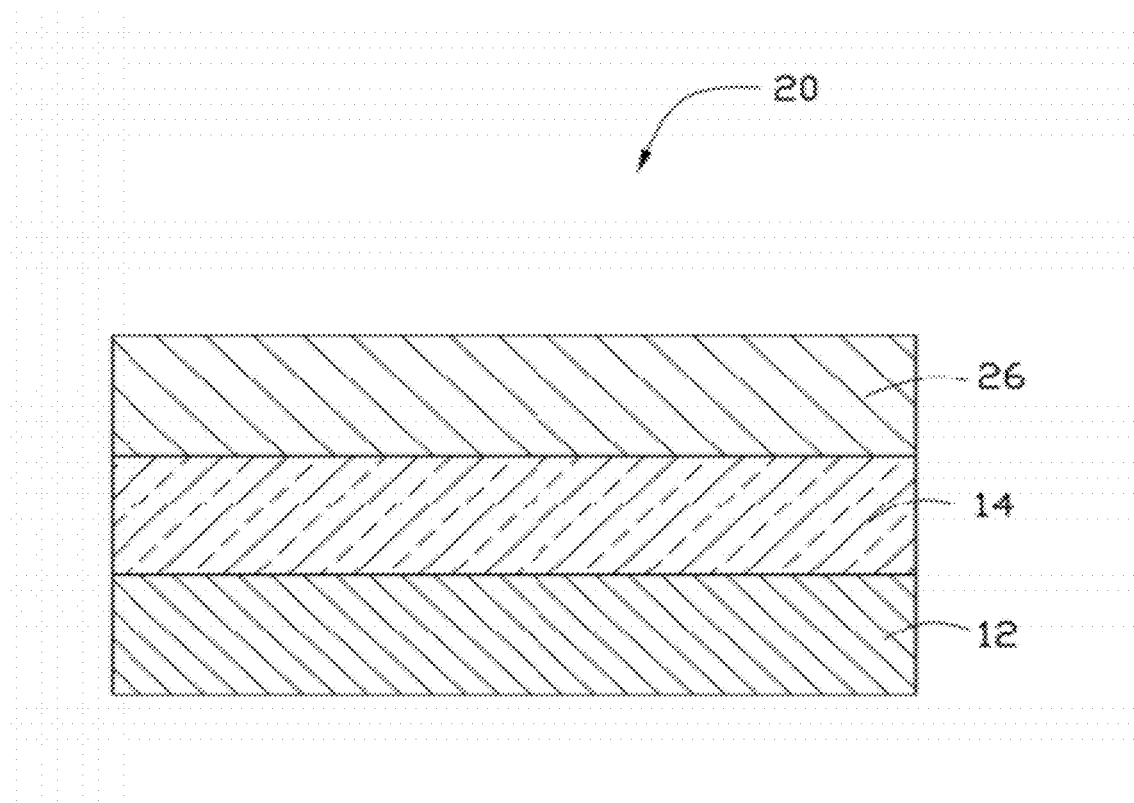
FIG. 10 is a cross-sectional view of another embodiment of a culture medium.

Referring to FIG. 10, one embodiment of a culture medium 20 includes a carbon nanotube structure 12, a hydrophilic layer 14, and a polar layer 26. The hydrophilic layer 14 is located on a surface of the carbon nanotube structure 12. The polar layer 26 is located on a surface of the hydrophilic layer 14 away from the carbon nanotube structure 12. In other words, the hydrophilic layer 14 is located between the carbon nanotube structure 12 and the polar layer 26.

The hydrophilic layer 14 makes the carbon nanotube structure 12 a hydrophilic environment for growing a number of neurons. In addition, the hydrophilic layer 14 makes the polar layer 26 adhere easily to the carbon nanotube structure 12. The thickness of the hydrophilic layer 14 is in a range from about 1 nanometer (nm) to about 100 nm. Preferably, the hydrophilic layer 14 has a thickness in a range from about 1 nm to about 50 nm. The hydrophilic layer 14 is made from inorganic materials, such as silicon dioxide, titanium dioxide, iron oxide, or any combination thereof. In one embodiment, the hydrophilic layer 14 is a silicon dioxide layer with a thickness about 10 nm.

The polar layer 26 is capable of providing a polarity such that the polarity of the culture medium 10 can attract the neurons. Thus, the culture medium 10 is capable of providing a bio-compatible environment for seeding the neurons and forming a nerve network. The surface of the culture medium 10 with a polarity will attract another polarity of a surface of the nerve network with the opposite affinity. Thus, the nerve network can closely adhere to the surface of the culture medium 10. A material of the polar layer 26 can be polyamino acid, polyetherimide, and any combination thereof. The polyamino acid can be poly-D-lysine (PDL). In one embodiment, the polar layer 26 is a PDL layer.

Figure 11:
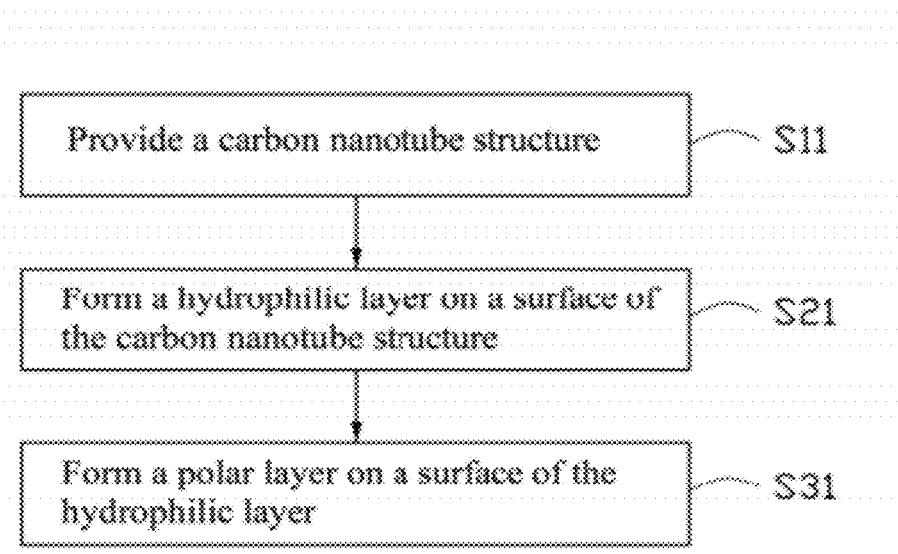
FIG. 11 is a flow chart of another embodiment of a method for forming a culture medium.

Referring to FIG. 11, a method for forming a culture medium includes the steps of:

S11, providing a carbon nanotube structure;

S21, forming a hydrophilic layer on a surface of the carbon nanotube structure; and S31, forming a polar layer on a surface of the hydrophilic layer to form the culture medium.

In the step S11, the carbon nanotube structure has a number of carbon nanotubes capable of forming a free-standing structure. The free-standing structure of the carbon nanotube structure is realized by the carbon nanotubes joined by van der Waals attractive force. The carbon nanotube structure can include at least one carbon nanotube film. The carbon nanotube film can be a flocculated carbon nanotube film as shown in FIG. 2, a pressed carbon nanotube film as shown in FIG. 2, or a drawn carbon nanotube film as shown in FIG. 4. In addition, the carbon nanotube structure can include at least one carbon nanotube wire. The carbon nanotube wire can be an untwisted carbon nanotube wire as shown in FIG. 6 or a twisted carbon nanotube wire as shown in FIG. 7. In one embodiment, the carbon nanotube structure is formed by 30 layers of drawn carbon nanotube films. The angle between the aligned directions of the adjacent drawn carbon nanotube films is substantially 90 degrees.

In the step S21, the hydrophilic layer is formed on the surface of the carbon nanotube structure by evaporation or sputtering. The material of the hydrophilic layer is hydrophilice. For example, the hydrophilic layer is made from inorganic materials, such as silicon dioxide, titanium dioxide, iron oxide, or any combination thereof. In one embodiment, the carbon nanotube structure formed by 30 layers of drawn carbon nanotube films is fixed at a frame, and then a silicon dioxide layer is formed on the surface of the carbon nanotube structure by electron beam evaporation.

In the step S31, the polar layer can be formed on the surface of the hydrophilic layer by the steps of:

(a1), providing a supporter;

(b1), placing the carbon nanotube structure having the hydrophilic layer on a surface of the supporter; and (c1), forming the polar layer on the carbon nanotube structure by soaking the carbon nanotube structure having the hydrophilic layer on the supporter.

In step (b1), the carbon nanotube structure can be located on part of the surface of the supporter. To decrease a specific surface area of the carbon nanotube structure and increase an adhesive attraction force between the carbon nanotube structure and the supporter, the step (b1) can further include the following steps: (b11), soaking the carbon nanotube structure on the surface of the supporter with an organic solvent; and (b12), evaporating the organic solvent from the carbon nanotube structure. In one embodiment, the supporter is a plastic petri dish or a watch dish.

In step (c1), the carbon nanotube structure can be soaked with a polyamino acid solution or a polyetherimide solution to form the polar layer. For example, the polyamino acid solution or the polyetherimide solution can be sprayed on the surface of the hydrophilic layer. In one embodiment, to soak the hydrophilic layer with the polyamino acid solution or the polyetherimide solution, the step (c1) includes a step of dripping the polyamino acid solution or the polyetherimide solution on the carbon nanotube structure having the hydrophilic layer on the supporter. In one embodiment, the polyamino acid solution is dripped on the carbon nanotube structure for about 10 hours. A concentration of the polyamino acid solution can be about 20 milligrams per milliliter.

The carbon nanotube structure having the polar layer can be further sterilized. Sterilizing the carbon nanotube structure having the polar layer kills nearly all of the bacteria distributed in the carbon nanotube structure. The carbon nanotube structure can be sterilized by means of an ultraviolet sterilization technology or a high temperature sterilization technology.

The culture medium including a carbon nanotube structure has the following benefits. First, the hydrophilic layer covers the surface of the carbon nanotube structure such that the culture medium has good hydrophilic property. Second, the carbon nanotube structure is capable of accommodating many different shapes. Third, both of the hydrophilic layer and the carbon nanotube structure can have good tactility, and nonmetal and bio-compatible properties. Thus, the culture medium including the hydrophilic layer and the carbon nanotube structure can be transplanted into a biological body and form a shape as desired.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A culture substrate, comprising:
a carbon nanotube structure comprising a pressed carbon nanotube film comprising a plurality of carbon nanotubes, an angle between a primary alignment direction of the carbon nanotubes and a surface of the pressed carbon nanotube film is about 15 degrees, and the carbon nanotube structure is a free-standing structure;
a hydrophilic layer directly located on a surface of the carbon nanotube structure, wherein the hydrophilic layer is configured to culture a plurality of neurons thereon such that the hydrophilic layer is located between the carbon nanotube structure and the plurality of neurons, a material of the hydrophilic layer is an inorganic material selected from the group consisting of silicon dioxide, titanium dioxide, iron oxide, and any combination thereof, and the hydrophilic layer has a thickness in a range from about 1 nm to about 50 nm; and a polar layer located on a surface of the hydrophilic layer away from the carbon nanotube structure, wherein the polar layer is made of polyetherimide.

2. The culture substrate of claim 1, wherein the carbon nanotube structure comprises at least one untwisted carbon nanotube wire.

3. The culture substrate of claim 1, wherein an area of the surface of the carbon nanotube structure is greater than 15×15 square millimeters.

\* \* \* \* \*